United States Patent [19]
Wolfinbarger, Jr.

[11] Patent Number: 6,024,735
[45] Date of Patent: Feb. 15, 2000

[54] PROCESS AND COMPOSITION FOR CLEANING SOFT TISSUE GRAFTS OPTIONALLY ATTACHED TO BONE AND SOFT TISSUE AND BONE GRAFTS PRODUCED THEREBY

[75] Inventor: Lloyd Wolfinbarger, Jr., Norfolk, Va.

[73] Assignee: LifeNet Research Foundation, Virginia Beach, Va.

[21] Appl. No.: 08/895,203

[22] Filed: Jul. 16, 1997

Related U.S. Application Data

[63] Continuation-in-part of application No. 08/619,412, Mar. 21, 1996, Pat. No. 5,820,581, application No. 08/620,856, Mar. 20, 1996, application No. 08/646,520, May 7, 1996, and application No. 08/646,519, May 7, 1996, Pat. No. 5,797,871, said application No. 08/619,412, is a division of application No. 08/395,113, Feb. 27, 1995, Pat. No. 5,556,379, said application No. 08/620,856, application No. 08/646,520, and application No. 08/646,519, which is a continuation-in-part of application No. 08/395,113.

[51] Int. Cl.$^7$ .................................................. A61M 31/00

[52] U.S. Cl. ............................. 604/500; 128/898; 623/16

[58] Field of Search ................................ 128/898; 604/28, 604/48, 49; 600/36; 623/16; 435/1, 267, 268

[56] References Cited

U.S. PATENT DOCUMENTS

| 5,095,925 | 3/1992 | Elledge et al. | 134/61 |
| 5,333,626 | 8/1994 | Morse et al. | 128/898 |
| 5,336,616 | 8/1994 | Livesey et al. | 435/240.2 |
| 5,513,662 | 5/1996 | Morse et al. | 128/898 |

*Primary Examiner*—Wynn Wood Coggins
*Assistant Examiner*—Deborah Blyveis
*Attorney, Agent, or Firm*—Susanne Hopkins

[57] ABSTRACT

The invention relates to compositions effective for the cleansing of mammalian soft tissue optionally attached to bones, and particularly the removal of blood deposits and bone marrow therefrom. The compsotions are composed of an aqueous solution containing as its essential ingredients a detergent having a functionality of the nature of a polyoxyethylene-23-lauryl either, a detergent having a functionality of the nature of exyethylated alkylphenol, and water, where the compositions are free from any membrane stabilizers. The present invention is also directed to a method and composition for cleaning cadaveric soft tissue optionally attached to bone to produce soft tissue grafts optionally attached to bone suitable for transplantation into a human. The present method involves removing bone marrow elements, blood deposits and any bacteria, virus or fungi contamination, from the donor bone and/or associated soft tissues.

28 Claims, No Drawings

600## PROCESS AND COMPOSITION FOR CLEANING SOFT TISSUE GRAFTS OPTIONALLY ATTACHED TO BONE AND SOFT TISSUE AND BONE GRAFTS PRODUCED THEREBY

REFERENCE TO RELATED APPLICATIONS

This application is a continuation-in-part of U.S. patent application Ser. No. 08/619,412, now U.S. Pat. No. 5,820,581 filed on Mar. 21, 1996 as a division of U.S. Ser. No. 08/395,113, filed Feb. 27, 1995, now issued as U.S. Pat. No. 5,556,379; U.S. patent application Ser. No. 08/620,856 filed on Mar. 20, 1996, which is a continuation-in-part of U.S. patent application Ser. No. 08/395,113, now issued as U.S. Pat. No. 5,556,379; U.S. patent application Ser. No. 08/646,520 filed on May 7, 1996, which is a continuation-in-part of U.S. patent application Ser. No. 08/395,113, now issued as U.S. Pat. No. 5,556,379; U.S. patent application Ser. No. 08/646,519, now U.S. Pat. No. 5,797,871 filed on May 7, 1996, which is a continuation-in-part of U.S. patent application Ser. No. 08/395,113, now issued as U.S. Pat. No. 5,556,379; the disclosures of which are incorporated herein in their entirety.

FIELD OF THE INVENTION

The subject invention relates to a composition and methods for the cleansing and disinfection of bones and/or associated attached or detached soft tissue, and cleansed bone and/or associated soft tissue produced thereby for use transplantation into a human.

BACKGROUND OF THE INVENTION

A major concern in the area of bone grafting technology is the effective and safe removal of bone marrow from the less solvent-accessible cancellous bone spaces within bone grafts.

For bone grafts, human bone may be obtained from cadaveric donors under sterile conditions in an operating suite environment of local hospitals. The bone is stored frozen until it is further processed into small grafts under similar sterile conditions, or under clean-room conditions. Procurement and processing of human tissues is typically performed by groups certified by the American Association of Tissue Banks under standard operating procedures for the processing of each specific bone graft. For instance, large bones such as the femur are thawed and debrided of excess tissue prior to being cut into smaller grafts.

Processing of small bones as well as smaller bone grafts obtained from large bones includes cleaning of bone marrow from the cancellous bone spaces using mechanical means, soaking, sonication, and/or lavage with pulsatile water flow under pressure.

Bone marrow elements include hematopoietic progenitor cells, i.e., those stem cells that will ultimately differentiate into red blood cells, white blood cells, and platelets, among others. These stem cells are rich in major histocompatibility antigens (i.e., MHC antigens) that function in immune responses. It is advantageous to have bone graft material which is essentially free of residual bone marrow, for use in the preparation of small bone grafts. Large, essentially whole, bone grafts with minimal residual bone marrow offer additional advantages in that removal of bone marrow, which may harbor potential viral particles and/or viral genomes integrated into the genomes of specific cell types present in the bone marrow, reduces the potential for transmission of infective agents such as bacteria and viruses, especially the human immunodeficiency virus (HIV), since cells capable of harboring the HIV virus are abundant in bone marrow. The removal of bone marrow from large or small bone grafts also reduces the bioburden of viruses which may be present within the bone marrow cells removed.

Conventional bone-cleaning protocols may include the use of detergents, alcohol, organic solvents or similar solutes or combination of solutes designed to facilitate solubilization of the bone marrow. Common methods may use reduced or elevated temperatures, for example, between 4° C. to 65° C.

Ethanol and detergents have been demonstrated to be bacteriocidal toward certain bacteria, such as gonorrhea, gram negative bacteria, for example, *Yersinia enterocolitica*, gram positive bacteria, for example, *Myobacterium tuberculosis* and Chlamydia, as well as acid fast bacteria. Ethanol and detergent solutions also offer advantages of enhancing solubilization of bone marrow, reducing surface tension properties of aqueous solutions, and inactivating viruses and bacteria.

Detergents are amphiphile compounds which facilitate solubilization of relatively insoluble lipids present in, for example, bone marrow, yet at high concentrations tend to form micellar structures (Helenius, A. and Simons, K., "Solubilization of Membranes by Detergents," *Biochim. Biophys. Acta* 415:29–79 (1975). The formation of micellar structures tends to limit the effective concentration range for detergent solutions, and thus, soaking of bone in a given volume of detergent solution may not be totally effective in that the absolute amount of detergent present is limited and if the amount of lipid material to be solubilized exceeds the solubilization capability of the detergent present, lipid solubilization will not be complete. By continually changing the detergent solution over time, it becomes possible to completely solubilize all solubilizable lipid present in bone graft.

Typically, hydrogen peroxide is used to oxidize the colored elements within the bone marrow, which results in a cleaner appearance. However, such bone often still contains bone marrow which is extremely immunogenic.

Further, most bone grafts are currently stored in the freeze-dried state. Freeze-drying removes water from the grafts, but lipid elements present in the membranes of the bone marrow cells and in vesicles present in adipocytes (i.e., fat storage cells) typically leak from the grafts after being placed in their final storage and distribution containers. These residues often give the appearance that the graft itself is not clean.

In fact, with conventional bone-cleaning protocols the graft often harbors bacteria, viruses and/or fungi in the bone marrow. Viruses, bacteria, and/or fungi may also be present in the soft tissues associated with bone.

Cleaning of bone marrow from small bone grafts (for example, tarsels and meta tarsels as small as 1–5 cm) has been described in the scientific literature and in brochures and documents made public by groups involved in the procurement and processing of human tissues. A for-profit public corporation, Cryolife, Inc. (Marietta, Ga.) promotes a bone cleaning process designated as VIP™ (Viral Inactivation Process) and claims that the process provides "Cleaner bone through mechanical removal of debris and tissue such as bone marrow, lipids and blood components" and "Safer bone through inactivation of pathogens such as HBV and HIV (greater than 5-log kill) as well as bacteria and fungi" (Cryolife Orthopedics, Inc., brochure 12, February, 1992;

Cryolife literature directed to Organ and Tissue Procurement Program Directors dated Feb. 20, 1992).

Minimal information regarding the methods of the process is available but it is described as a multi-step approach having three phases: 1) preliminary surface disinfection of procured tissue for the protection of processing technicians during thawing, debriding and cutting; 2) cleaning and removal of debris from the cut pieces with a surfactant at elevated temperature; and 3) terminal disinfection of the cleaned bone grafts (The Viricidal Capacity of a Surfactant/Iodophor-Based Viral Inactivation Process for Bone Allografts, Cryolife documentation). The VIP process is claimed to both clean bone allografts, e.g., a femur head, and to inactivate a variety of bacteria and viruses without affecting bone strength or biological properties. However, according to documents made public by Cryolife, Inc., the process is used to clean the surfaces of large bone grafts and to remove bone marrow from the cancellous bone spaces of small bone grafts cut from the larger grafts.

A second, for-profit publicly held corporation, Osteotech, Inc., Shrewbury, N.J., describes a bone graft cleaning process called Permein ("a combination of ethanol and nonionic detergent"; Mellonig, J. T., Prewett, A. B., and Moyer, M. P., *J. Periodontal* 63:979–983 (December, 1992). This Process involves the use of a solution of ethanol and detergent to clean bone grafts. Details of the process and detergents utilized are not currently available. Bone is soaked in the solution and it is claimed that the combination of ethanol and detergent facilitates permeation of the solution into bone. The process has been demonstrated to clean small cut-bone grafts and to be capable of inactivating the HIV in bone allograft (finely ground bone).

SUMMARY OF INVENTION

The invention addresses the deficiencies and problems in the prior art by novel compositions which contain a detergent having a functionality of the nature of a lauryl ether, and a detergent having a functionality of the nature of oxyethylated alkylphenol, which are quite effective in removing bone marrow from bones and bone grafts. The detergents are effective in the formation of micelles containing bone marrow particles and/or debris. The concentration of the detergents is such that the bone marrow particles and/or debris are (1) completely solubilized and (2) kept in solution. In this fashion, the concentration of the particles and/or debris is reduced to below the critical micelle concentration value (CMC). (Critical micelle concentration is a fixed number, and values are assigned to detergents based on their respective detergent properties and the molecular weights at which they function as detergents.) Thus, the particles and/or debris are in monomeric form so as to be easily washed out of the bone graft.

The compositions of the invention comprise a superior, safe, non-toxic, non-pyrogenic solvent and detergent based aqueous agent that effectively solubilizes and removes bone marrow from bone. The invention penetrates the less solvent accessible cancerous spaces within the bone grafts, thus providing effective removal of bone marrow in one easy and quick cleansing step. Bone grafts cleaned with the inventive composition retain bone inductive properties while the bone marrow debris is quickly solubilized and removed. Bone marrow removal reduces the bioburden of viruses, bacteria and fungi which grow and may be present in the bone marrow. The compositions of the present invention also reduce the viral load of soft tissues associated with, attached to, or removed from bone, to an undetectable level. These compositions further reduce the immunogenicity of associated soft tissues.

In addition, the compositions of the invention are easily removed by a simple washing procedure, and virtually no residual detergents are present in the bone after washing. The compositions of the invention are an improvement over the art in providing easy-to-use excellent cleaning power at a low cost.

Well balanced optimized low concentrations of nonionic and ionic surfactants and detergents of the invention act synergistically to lyse, solubilize and keep in solution proteins, lipids, hemopoietic progenitor cells, red blood cells, white blood cells, platelets and histocompatible antigens. The surfactants preferably include Nonoxynol-9, (a known anti-HIV agent), Brij-35 (protein solvent), Tergitol NP-40 (a lipid solvent) and IGEPAL CA 630. These surfactants are provided as micelles in optimized critical micelle concentrations (CMC) to dissolve bone marrow particles and/or debris, which after being consumed in the cleansing process, are reduced to a concentration below the CMC value. At that concentration level the particles and/or debris are in monomeric form (i.e., act as monomers), and can subsequently be easily removed via washing steps, leaving no detectable residues in the bone.

Accordingly, objects of the invention include the development of compositions which are effective for the cleaning and disinfecting of bones and/or associated soft tissue, such as by facilitating the removal of bone marrow and other blood deposits from the interstitial lumen and cancellous bone space of bone and from soft tissue.

Another object of the present invention is to provide a bone cleaning composition which removes most or substantially all of the bone marrow elements from bone grafts with minimal handling and processing, to reduce the risk of viral, bacterial and fungal transmission.

It is a further object of the invention to provide a composition which improves solvent penetration into and through the bone and/or associated soft tissue and increases the solubility of bone marrow and/or blood deposits, facilitating their removal from the bone.

Another object of the present invention is to provide a method for cleaning a soft tissue graft optionally attached to bone, by subjecting the soft tissue to a negative pressure environment.

An object of the present invention is to provide a method for producing a soft tissue graft optionally attached to bone suitable for transplant into a human by subjecting the soft tissue optionally attached to bone to a pressure mediated flow of solution.

An object of the present invention is to provide a method for producing a soft tissue graft optionally attached to bone suitable for transplant into a human by subjecting the soft tissue optionally attached to bone to a negative pressure mediated flow of solution.

An object of the present invention is to provide a method for producing a soft tissue graft optionally attached to bone suitable for transplant into a human by sonicating the soft tissue optionally attached to bone with one or more cleaning solutions.

An object of the present invention is to provide a method for producing a soft tissue graft optionally attached to bone suitable for transplant into a human by incubating the soft tissue with on e or more cleaning solutions.

A yet further object of the invention is to provide methods and composition for the reduction of the immunogenicity and viral load of bone and/or associated soft tissues without adversely affecting the biological and biomechanical properties thereof.

An object of the present invention is to provide a method for producing a soft tissue graft optionally attached to bone suitable for transplant into a human by subjecting the soft tissue optionally attached to bone to a pressure mediated flow of solution where the solution is recirculated through the bone via the pressure mediated flow.

These and other objectives of the instant invention have been realized by use of an aqueous composition which contains as its essential ingredients a detergent having a functionality of the nature of a lauryl ether, a detergent having a functionality of the nature of oxyethylated alkylphenol, and water. The detergent having a functionality of the nature of a lauryl ether and the detergent having a functionality of the nature of oxyethylated alkylphenol should preferably be present in a weight percent ratio of about 3:2:2, respectively.

Preferably, the detergent having a functionality of the nature of oxyethylated alkylphenol consists of a combination of two compounds selected from the group consisting of poly(ethylene glycol)-p-nonyl-phenyl-ether, octylphenol-ethyleneoxide, polyoxyethylene alcohols, polyethylene glycol p-isooctylphenylethers, polyoxyethylene nonylphenol and polyoxyethylene sorbitol esters. Poly(ethylene glycol)-p-nonyl-phenyl-ether and octylphenol-ethyleneoxide are the preferred two compounds. The detergent having a functionality of the nature of a lauryl ether and the two compounds are preferably present in a weight percent ratio of about 3:1:1, respectively.

In one embodiment, the invention relates to bone cleansing compositions containing as essential components i) between about 0.001 to about 2 weight percent (more preferably from about 0.01 to about 0.5 weight percent and most preferably, about 0.066 weight percent) of a detergent having a functionality of the nature of a lauryl ether (such as lauryl ether itself, preferably polyoxyethylene-4-lauryl ether, and more preferably one of the Brij series), ii) between about 0.001 and about 2 weight percent (more preferably from about 0.01 to about 0.5 weight percent and most preferably about 0.04 weight percent) of a detergent having a functionality of the nature of oxyethylated alkylphenol, (such as oxyethylated alkylphenol itself, preferably poly(ethylene glycol)-p-nonyl-phenyl-ether and/or octylphenol-ethyleneoxide, and more preferably Nonoxynol-9 and/or Tergitol NP-40, and/or IGEPAL CA 630), and iii) water (preferably endotoxin-free deionized/distilled water).

Preferably, the detergent having a functionality of the nature of oxyethylated alkylphenol consists of a combination of two compounds selected from the above-referenced group. The two compounds are preferably each present in about 0.02 weight percent.

In a preferred embodiment, the invention relates to bone cleansers composed of an aqueous solution containing as its essential ingredients i) about 0.066 weight percent polyoxyethylene-4-lauryl ether, ii) about 0.02 weight percent poly(ethylene glycol)-p-nonyl-phenyl-ether (such as, preferably, Nonoxynol-9), iii) about 0.02 weight percent octylphenol-ethyleneoxide (such as, preferably, Tergitol NP-40) or IGEPAL CA 630; and iv) water (preferably, endotoxin-free deionized/distilled water).

In another embodiment, the invention also relates to a kit for cleaning a bone for a bone graft, comprising a solution containing one or more of the above-described compositions. The kit may optionally include instructions such as instructions for dilutions necessary to obtain appropriate weight percentages of the components in an aqueous solution.

DETAILED DESCRIPTION OF THE PREFERRED EMBODIMENTS

I. Definitions

The below definitions serve to provide a clear and consistent understanding of the specification and claims, including the scope to be given such terms.

Agitation. By the term "agitation" is intended any method of agitation including mild and vigorous agitation. Agitation may be carried out in a negative pressure environment.

ALLOWASH™ Solution. By the term "ALLOWASH™ solution" is intended those compositions disclosed in co-pending U.S. patent application Ser. No. 08/620,856 incorporated herein by reference. Examples of suitable ALLOWASH™ compositions include: a cleaning composition containing essentially about 0.06 weight percent (wt. %) polyoxyethylene-4-lauryl ether; about 0.02 wt. % poly (ethylene glycol)-p-nonyl-phenyl-ether; about 0.02 wt. % octylphenol-ethyleneoxide and endotoxin free deionized/distilled water.

Blood Deposits. By the term "blood deposits" is intended blood cells including red blood cells, white blood cells and platelets and including MHC antigens, and potential viral, bacterial, and fungal contamination present in soft tissue associated with bone.

Bone Graft. By the term "Bone Graft" is intended any bone or piece thereof obtained from a cadaver donor, for example any essentially intact bone including for example the femur, tibia, ilia, humorous, radius, ulna, ribs, whole vertebrae, mandibula and/or any bone which can be retrieved from a donor with minimal cutting of that bone for example, one half of an ulna, a femur cut in half to yield a proximal half and a distal half, and/or at least a substantial portion of a whole bone, i.e. at least one-quarter of a whole bone; and/or any small cut pieces of bone, for example, iliac crest wedges, ground bone, Cloward dowels, cancellous cubes, and/or fibular struts.

Bone Marrow or Bone Marrow Elements. By the term "bone marrow" or "bone marrow elements" is intended for the purposes of the present invention the highly cellular hematopoietic connective tissue filling the medullary cavities and spongy epiphyses of bones which may harbor bacterial and/or viral particles and/or fungal particles.

Decontaminating Agent. By the term "decontaminating agent" is intended one or more agents which remove or inactivate/destroy any infectious material potentially present in the bone marrow of a bone graft, for example, such materials including but not limited to: bacteria, virus, and/or fungi; with such decontaminating agents including, for example, but not limited to one or more of the following: an antibacterial agent; an antiviral agent; an antimycotic agent; an alcohol for example, methyl, ethyl, propyl, isopropyl, butyl, and/or t-butyl; peracetic acid; trisodium phosphate; sodium hydroxide; hydrogen peroxide; EXACT™ (a product of ExOxEmis, Inc., Tex.) and/or any detergent.

Detergent. By the term "detergent" is intended any agent which through a surface action that depends on it possessing both hydrophilic and hydrophobic properties and/or exerts oil-dissolving (cleansing) and/or antibacterial and/or antiviral effects, and can include but is not limited to: anionic detergents, nonionic detergents, cationic detergents, acridine derivatives, long-chain aliphatic bases or acids, and the present ALLOWASH™ solution. Examples of specific detergents include: (i) Nonoxynol including Poly (ethylenegylcol) P-Nonyphenyle ether including Nonylphenoxypolyethoxyethanol; (ii) Nonidet p.40 including Igepal CA-630, Antarox A-200 and Triton X-100 (b-octylphenoxyethanol), including Polyethylene Glycol p-isonctylphenyl Ether including octylphenoxypolyethoxyethanol and (4-(1,1,3,3-tetramethyl 1 butylphenyl)-00-hydroxy poly (oxy 1,2 ethanediyl); (iii) Brio including a polyoxyethylene ether and Bru35 including Polyoxyethylene-23-Lauryl Ether.

Essentially Free From. By the term "essentially free from" is intended a bone graft where the material removed (i.e., bone marrow, viral, fungal, and/or bacterial particles) from the bone graft is not detectable using detection means known in the art at the time of filing of this application.

Essentially Intact Bone Graft. By the term "essentially intact bone graft" is intended for the purposes of the present invention any whole bone including, for example, the femur, tibia, ilia, humorous, radius, ulna, ribs, whole vertebrae, mandibular, and/or any bone which can be retrieved from a donor with minimal cutting of that bone, for example, one half of an ulna, a femur cut in half to yield a proximal half and a distal half, and/or at least a substantial portion of a whole bone, i.e., at least one-quarter of a whole bone.

Mild Agitation. By the term "mild agitation" is intended agitation achieved through the use of a gyrator shaker or means to achieve a similar result, including, for example: low pressure pulsatile lavage wherein induced currents in the solution impact the surface of bone and associated soft tissue.

Negative Pressure. By the term "negative pressure" is intended for the purposes of this invention a pressure below atmospheric pressure, i.e., less than one atmosphere.

Negative Pressure Environment. By the term "negative pressure environment" is intended a gaseous or liquid environment under negative pressure including, for example, a negative pressure air atmosphere, and a liquid environment under negative pressure. A negative pressure environment in the context of the present invention means that the soft tissue optionally including bone is, for example: itself exposed to a negative pressure gaseous atmosphere or is placed in a container of solution which container is placed under negative pressure where the tissue is partially or fully immersed in the solution.

Positive Pressure. By the term "positive pressure" is intended for the purposes of this invention a pressure at or above one atmosphere, i.e., greater than or equal to one atmosphere.

Pressure Mediated Flow of Solvent. By the term "pressure mediated flow of solvent" is intended for the purposes of the present invention a flow of solvent induced by positive or negative pressure.

Soft Tissue. By the term "soft tissue" is intended soft tissues associated with bone regardless of whether they are directly attached to the bone. Examples of associated soft tissue attached to bone include, but are not limited to, periosteum, cartilage, tendons and ligaments. Examples of associated soft tissue not attached to bone include, but are not limited to, menisci and *fascia lata*.

Solvent. By the term "solvent" is intended for the purposes of the present invention, a liquid cleaning composition capable of: facilitating the solubilization of lipid, facilitating bone marrow removal, inactivating viral and/or bacterial particles, and/or disrupting cell membranes, which may contain, but is not limited to, one or more of the following: sterile water; saline; a detergent; an alcohol, for example, ethanol and/or isopropanol, solvents, a combination of solutes desired to facilitate solubilization of bone marrow including for example, one or more of: the present bone cleaning solutions including ALLOWASH™ solution disclosed in co-pending patent application Ser. No. 08/620,856 herein incorporated by reference; a chelating agent; a virucidal agent; bacteriocidal agent; antimycotic agent; sodium hydroxide; or similar strong base; organic and/or inorganic acids; and hydrogen peroxide.

Ultrasonic Cleaner. By the term "ultrasonic cleaner" is intended any ultrasonic cleaning device capable of operating at: from 20 kHz to 50 kHz, preferably from about 40 kHz to about 47 kHz, and includes, for example, Branson ultrasonic cleaner model nos.: 1210, 2210, 3210, 5210 and 8210; or any similar ultrasonic cleaner. Sonication may be carried out in a negative pressure environment.

Vigorous Agitation. By the term "vigorous agitation" is intended agitation achieved through the use of a commercial paint can shaker or other means which achieve a similar result including, for example, high pressure pulsatile lavage wherein induced currents in the solution impact the surface of bone and associated soft tissue.

II. Cleaning Compositions

The bone cleaning compositions according to the present invention result in the effective removal of substantially all of the bone marrow elements within the cancellous bone spaces of bone grafts optionally having associated soft tissues. The associated soft tissues include attached soft tissues such as tendons, periosteum, cartilage and ligaments either attached or removed for cleaning, and non-attached soft tissues such as *fascia lata* and menisci. The bone cleaning composition is effective to remove most or substantially all of the bone marrow elements from large and small bone grafts with minimal handling and processing, while reducing the risk of viral, bacterial and fungal transmission.

The components of the invention should be non-toxic and/or leave a non-toxic residual concentration of materials in the bone after flushing with the second solution. In particular, following cleaning of bone grafts, it is necessary that residual detergents or other components which may remain associated with the bone graft are not toxic towards human fibroblast cells expected to migrate into the bone graft material(s) following implantation.

As explained above, in order that the composition be effective for the cleansing of bones, and in the removal of bone marrow and like blood deposits, the composition should be composed of an aqueous solution containing as its essential ingredients water (such as, preferably, endotoxin-free deionized/distilled water), and at least two detergents: a detergent having a functionality of the nature of a lauryl ether, and a detergent having a functionality of the nature of oxyethylated alkylphenol/polyethylene glycol phenyl ether.

The lauryl ether-functioning component should be present at between about 0.001 to about 2 weight percent, more preferably from about 0.01 to about 0.5 weight percent, and most preferably about 0.066 weight percent. The polyehtylene glycol phenyl ether-functioning component should be present at between about 0.001 to about 2 weight percent, more preferably from about 0.01 to about 0.5 weight percent, and most preferably about 0.04 weight percent. In other words, the lauryl ether-functioning component and the polyethylene glycol phenyl ether-functioning component are present in a weight percent ratio of about 1.65:1, respectively.

The lauryl ether-functioning component may itself be a lauryl ether, which may be selected from the group consisting of polyoxyethylene-23-lauryl ether (such as Brij series, Lubrol W, etc.), polyoxyethylene (9) lauryl ether (such as $C_{12}H_{18}$), polyoxyethylene (9) lauryl ether (such as $C_{12}H_{18}$), dodecylmaltoside lauryl maltoside (such as dodecyl β-D-maltopyramoside), decaoxyethylene monolauryl ether (such as GENAPOL C-100), octaethylene glycolisotridecyl ether (such as GENAPOL X-080), polyoxyethylene (8) isotridecyl ether (such as GENAPOL X-080), polyoxyethylene (10) isotridecyl ether (such as GENAPOL X-100), PEG (10) tridecyl ether (such as GENAPOL X-100), sodium lauryl sulfate, and sodium dodecyl sulfate.

The lauryl ether-functioning component may be available in a less concentrated form, such as Brij-35, which is the equivalent of a 35% solution of polyoxyethylene-4-lauryl ether. In such a case, the weight percent of Brij-35 in the composition of the invention should be adjusted so that the final weight percent ratio is 0.066 weight percent Brij-35: 0.04 weight percent polyethylene glycol phenyl ether-functioning component. This is further explained in the examples below.

The polyethylene glycol phenyl ether-functioning component may itself be polyethylene glycol phenyl ether, which may be selected from the group of consisting of poly(ethylene glycol)-p-nonyl-phenyl-ether, octylphenol-ethyleneoxide, polyoxyethylene alcohols, polyethylene glycol p-isooctylphenylethers (such as Triton X series), polyoxyethylene esters, 1-argitol, polyoxyethylene nonylphenol, and polyoxyethylene sorbitol esters (such as Tween series and Emasol series).

It is preferable that the polyethylene glycol phenyl ether-functioning component consists of two compounds selected from the group consisting of poly(ethylene glycol)-p-nonyl-phenyl-ether, octylphenol-ethyleneoxide, and polyoxyethylene alcohols, polyethylene glycol p-isooctylphenylethers, polyoxyethylene nonylphenol, and polyoxyethylene sorbitol esters. More preferably, the compounds are poly(ethylene glycol)-p-nonyl-phenyl-ether and octylphenol-ethyleneoxide. Preferably, the two compounds are each present in 0.020 weight percent. That is, the lauryl ether-functioning component and the two compounds are preferably present in a weight percent ratio of about 3.3:1:1, respectively.

In a preferred embodiment, the solution includes ALLO-WASH™ solution, available from LifeNet Research Foundation, 5809 Ward Court, Virginia Beach, Va. 23455, ALLOWASH™ solution contains three detergents, i.e., (1) Brij-35 (more specifically, polyoxyethylene-r-lauryl ether having the chemical formula $C_9H_{19}(OCH_2CH_2)_4OH$), (2) Tergitol NP-40 (sometimes known as Nonidet P-40 or NP-40) having the chemical name octylphenol-ethyleneoxide or IGEPAL® CA 630, and (3) Nonoxynol-9 having the chemical name poly(ethylene glycol)-p-nonyl-phenyl-ether or IGEPAL® CO 630.

Polyoxyethylene-4-lauryl ether is useful in that it acts as a protein solubilizing detergent and is used extensively in electrophoreses of proteins where additional charge problems might affect separation. Thus, in the cleaning solutions of the invention, polyoxyethylene-4-lauryl ether is believed to serve in enhancing solubility of the bulk proteins in the bone marrow, keeping them "in solution" once solubilized.

Octylphenol-ethyleneoxide and poly(ethylene glycol)-p-nonyl-phenyl-ether are useful in solubilizing membranes from cell (plasma) membranes. Thus, in the cleaning solutions of the invention, octylphenol-ethyleneoxide and poly (ethylene glycol)-p-nonyl-phenyl-ether are believed to serve primarily in literally solubilizing the plasma membranes of the bone marrow cells.

It is important in this invention that at least one of the detergents be present in a concentration above its critical micelle concentration. Detergents are typically evaluated based on their "critical micelle concentration" (CMC). The CMC is that concentration of detergent in solution where free molecules or detergent begin to aggregate into micellar structures. In the cleaning compositions of the invention, the concentration of at least one of the detergent components should exceed its CMC so that there is sufficient detergent available in the solution to have micelles present in the solution to replenish monomeric detergent as it is consumed in bone marrow solubilization. Notably, however, the invention is still effective in cleaning bones if the concentration of one or two of the detergents (especially octylphenol-ethyleneoxide or Tergitol NP-40) drops below its CMC. For example, if the cleaning solution becomes diluted.

For Brij-35, the published CMC is approximately 0.092 mM (millimolar) and was experimentally determined (by detergent mediated solubilization of an "insoluble" dye) to be about 0.09 mM±0.026 mM; for Nonoxynol 9, the published CMC is approximately 0.0812 mM and was experimentally determined to be about 0.062±0.008 mM; and for Nonidet P-40, the published CMC is approximately 0.11 to 0.29 mM and was experimentally determined to be about 0.234±0.005 mM. For this invention, the higher CMC values reflect greater effectiveness in cleaning bone grafts, because after the bone marrow particles and/or debris are "consumed" into micelles their concentration falls below the CMC values and they are in soluble monomeric form.

The bone cleaning solution can include about 0.0001× to 10× of a 1× detergent solution containing about 0.066 weight percent polyoxyethylene-4-lauryl ether (about 0.066 weight percent Brij-35), about 0.020 weight percent Tergitol NP-40, and about 0.020 weight percent Nonoxynol-9 in endotoxin free water (such as ALLOWASH™ solution, where Brij-35 is preferably used). Preferably, the solution comprises about 0.001× to 0.1× of the 1× detergent solution, and more preferably, about 0.00× to 0.01× of the 1× detergent solution, and most preferably, about 0.005× to 0.01× of the 1× detergent solution.

A 0.01× concentration of the ALLOWASH™ solution includes a solution of 1 ml of the 1× solution in 99 ml of endotoxin free water, and other solutions comprise corresponding dilutions and/or concentrations thereof At a 0.01× concentration of ALLOWASH™ solution, all three detergents are above their critical micelle concentrations (Brij-35 concentration is 0.55 mM, Non-9 concentration is 0.32 mM, and NP-40 concentration is 0.33 mM).

For example, a 0.01× solution includes a solution of 1 ml of the 1× solution in 99 ml of endotoxin free water to provide a solution comprising 0.00066 weight percent Brij-35, about 0.0002 weight percent Nonidet P-40, and about 0.0002 weight percent Nonoxynol-9 in endotoxin free water, and a 10× solution comprises 0.66 weight percent Brij-35, about 0.2 weight percent Nonidet P-40, and about 0.2 weight percent Nonoxynol-9 in endotoxin free water.

Formulations including solutions of detergents of Brij-35, Nonidet P-40, and Nonoxynol-9 are disclosed in U.S. patent application Ser. No. 08/395,113, filed Feb. 27, 1995. U.S.

patent application Ser. No. 07/696,955 discloses these detergents in combination with membrane stabilizers. Both foregoing applications are hereby incorporated by reference especially for their disclosure concerning detergents that are effective in reducing or killing microorganisms and viruses in a relatively short period of time.

In accordance with the present invention, the bone cleaning compositions can include concentrations of about 0.0001× to 10×, preferably 0.001× to 0.1×, more preferably 0.001× to 0.01× and most preferably 0.005× to 0.01×. As discussed above, these solutions should preferably be at a concentration so that upon completion of cleaning of the bone, e.g., prior to implantation, the concentration of detergents and/or any of materials in the solution is below a toxic level. For example, a 0.01× solution is a preferred solution, because removal of 90 percent of this solution from the bone, such as by subsequent flushing with secondary solutions, reduces the concentration to approximately a 0.001× solution, which is the non-toxic level. Thus, a 0.01× solution provides a highly cost effective solution having an effective concentration of detergents without wasting excess detergents.

Optionally, the solution may include alcohols, such as ethanol. Alcohols are advantageous in that they improve the action of the cleaning solution of the invention as a bone marrow solubilizing agent. For instance, ethanol, when included, is included in a solution of about 5 to 95% ethanol, measured by a volume-to-volume ratio, and more preferably in the range of about 10 to 30% ethanol, measured by a volume-to-volume ratio.

The cleaning solutions of the present invention can include any extraneous components in amounts that are not detrimental to the cleaning of the bone. For example, components that may be a detrimental contaminant at higher concentrations can be non-toxic and/or without consequence to the cleaning efficiency of the cleaning solution at lower concentrations.

Further, the cleaning solution may include at least one component selected from the group consisting of antibiotics, antiviral agents (for example, peroxide generating agents such as EXACT™ (e.g., trademarked haloperoxidase products marketed by ExOxEmis, Inc., San Antonio, Tex.)), hydrogen peroxide, permeation enhancers (for example, fatty acid esters, such as laurate, myristate and stearate monoesters of polyethylene glycol), organic acids (for example, citric acid) or dilute solutions of strong acids (for example, hydrochloric acid).

It is advantageous to clean bones using at least two separate solutions of the invention. For instance, a first cleaning solution can include about 0.01× of the 1× detergent solution. After the first solution is applied to the bone, a second solution may be used for flushing the first solution from the bone and for further reducing bacterial, fungal or viral contaminants. Preferably, the second solution includes at least one component selected from the group consisting of endotoxin-free deionized/distilled water and ethanol. Further, the second solution may include at least one component selected from the group consisting of antibiotics, antiviral agents, hydrogen peroxide, permeation enhancers, organic acids and dilute solutions of strong acids.

The solutions of the invention are preferably controlled within a temperature range of 20° C. to 65° C. and maintained within the temperature range during processing. More preferably, the temperature range is controlled and maintained at about 27° C. to 55° C. Even more preferably, the temperature range is controlled and maintained at about 40° C. to 48° C.

The compositions of the invention are useful with any type or size of bone and/or attached on unattached associated soft tissue, in whole or in part. Although the examples below describe use of the invention on "large" bone grafts, the compositions of the invention are also useful for the cleaning of any bone or portion of bone, regardless of size. Further, the examples are directed especially to human cadaveric bones, but it should be understood that the invention is equally applicable to bones and soft tissue obtained from other species.

As used herein, the terms "bone" or "bone graft" may be used interchangeably, and include whole, intact bones, regardless of size, or substantial parts of a whole bone with or without associated soft tissue, or associated soft tissue itself Practically speaking, bones or bone grafts, as defined herein may include the range of whole bones down to pieces at least as small as 1–5 cm. Examples of whole bones include (but are not limited to) femur, tibia, ilia, humerus, etc., prior to subsequent processing into specific grafts and may include associated soft tissues.

The composition of the invention is viricidal towards enveloped viruses such as the HIV, hepatitis, and herpes viruses, for example. Further viruses which have been killed by the instant compositions include measles virus, togavirus, enterovirus, rhinovirus, rubella virus, reovirus, respiratory syncytial virus, cytomegalovirus, Epstein Barr Virus, Vesicular Stomatitis Virus, vaccinia virus, rabies virus, influenza virus, parainfluenza virus, adeno-associated virus, lymphoma virus, human papovirus, and lymphocytic choriomeningitis virus, for example.

It is possible to monitor the solution exiting the bone cavity to determine when essentially all of the bone marrow has been removed from the bone. Monitoring methods include, but are not limited to, measuring absorbance substantially at 410 nm, and visual monitoring of the color of the solution exiting the bone.

Other methods of determination of the degree to which the bone marrow has been removed from the bone graft include: taking core samples of bone plugs, solubilizing bone marrow in the bone plug core samples using sodium hydroxide and taking a protein assay of the same. Visual inspection of the trabecular bone can be examined using a scanning electron microscope. Gross visual examination can be performed by cutting the graft open for visual inspection by the naked eye or with a stereoscope, for example.

III. Soft Tissue Cleaning Processes in Which the Compositions of the Invention May Be Used Attached soft tissues (e.g., ligaments, periosteum, cartilage and tendons) that are attached to bone or removed from the bone; and soft tissues (*fascia lata* and menisci) that are associated with but not attached to bone, can be exposed to detergent solutions including ALLOWASH™ without altering the biomechanical properties of these soft tissues. Under these conditions, viruses are inactivated. Cleaning associated soft tissue attached to the bone, or cleaning the associated soft tissue itself, does not alter the tissues tensile properties. These soft tissue may be treated with a viricidal agent. Therefore, soft tissue cleaned of blood deposits (with or without associated bone) for use in clinical applications are prepared.

The detergents present in the ALLOWASH™ solution are capable of dissolving membranes of cells and soluble low molecular weight proteins present in those cells. It can also solubilize low molecular weight proteins associated with the less soluble collagens/elastins. Thus, the present invention also includes a method for producing bone grafts cleaned of bone marrow with associated soft tissue which soft tissue is not altered in its tensile properties and which has been treated with a viricidal agent and is of reduced immunogenicity and has reduced viral load.

A. Pressure Mediated Flow of Solution

The compositions of the invention may be used in a variety of soft tissue cleaning procedures where the soft tissue is attached to bone. For instance, the solutions may be utilized in conventional flushing procedures to remove blood deposits and bone marrow, which entails a pressurized flow of solution as a rapidly moving stream which dislodges blood deposits and bone marrow by impact of the solvent on the soft tissue and bone graft.

The compositions may also be used in a process such as the following. Bone materials procured from cadaveric donors, such as large, essentially whole, bone grafts, are thawed under sterile conditions at room temperature. The bone is then debrided of excess cartilaginous tissues on the proximal and distal ends of bones at their articulation surfaces.

Thereafter, a hole is made substantially midway between the distal and proximal ends of the bone. The hole may be formed by drilling, and is preferably formed to have an outside diameter of approximately ¼ to ⅝ inch. The hole need only be drilled deep enough to penetrate the cortical bone to enable a tapping port to be securely inserted into the hole. After removing as much bone marrow as possible, a vacuum line is attached securely at one end to the tapping port after insertion of the tapping port into the hole.

The opposite end of the vacuum line is securely attached to a disposable container, via an inlet tube. The inlet tube is sealingly connected to a disposable container by a stopper means. The stopper means is preferably a rubber stopper, but any equivalent, such as, a plastic or cork stopper, may be used to seal the inlet tube within the disposable container.

An outlet tube of the disposable container is securely attached to another vacuum line. At the opposite end, the vacuum line is attached to a vacuum source which is capable of drawing a vacuum in the range of about 5 inches to 30 inches Hg vapor on the entire apparatus. The vacuum source used to draw solution through the bone grafts will be set to draw a vacuum between about 15 and 35 inches Hg vapor with the preferred range being about 20 and 30 inches Hg vapor.

After connection of the vacuum apparatus, the bone is immersed into a solvent containing one of the compositions of the invention, contained within an open container. The vacuum source is next turned on to draw the solution through the articulating surfaces which have been debrided of cartilage as necessary, through the cancellous bone structure and through the intermedullary canal of the bone.

As mentioned above, the vacuum drawn is set between about 15 and 35 inches Hg vapor with the preferred range being between about 20 and 30 inches Hg vapor. The actual vacuum level is adjusted such that the flow rate of solution through the bone graft does not occur so rapidly that the bone marrow is not effectively solubilized, but rapidly enough to effectively remove solubilized bone marrow. Flow rates of solvent should range between about 8 and 32 ml per minute with the preferred rates being between about 15 and 25 ml per minute.

The solution enters the bone through the ends at the cartilaginous surfaces. Restricted flow of the solution through the cartilaginous ends of the bone minimizes mechanical and/or structural damage to the cancellous bone by causing a slow flow rate of solvent through the trabecular bone space occupied by bone marrow. As the solution is drawn through the bone, it can be collected in a disposable container. Because the aspirate solution is largely liquid phase, the solution is deposited into the disposable container as the vacuum is drawn through the inlet tube end out the outlet tube.

The process may optionally include refilling the container with a second solution for further processing the bone including flushing the first solution from the bone. The second solution is drawn through the cartilaginous articulating surface and then through the bone cavity and the vacuum line to exit the bone at the opening. Optionally the second solution may be recirculated through the bone and associated soft tissue.

The solution is collected in the disposable container and is initially dark red, reflecting a saturated or nearly saturated solution of marrow. As the process continues, the solution gradually turns to a color similar to that of serum as bone marrow is removed from the graft. By sampling the effluent material being removed from the bone, such as by a sampling port accessible by use of a syringe, it is possible to monitor completion of bone marrow removal by measuring absorbance at 410 to 700 nm. By this method, it is possible to determine when essentially all of the bone marrow is removed from the bone graft. Bone marrow solubilization and cleaning of the bone is essentially complete when eluent protein concentration reaches a minimal, substantially stable value.

After it has been determined that essentially all of the bone marrow has been removed from the bone (i.e., the bone graft) the bone is removed from the container and the solution can be replaced with a second solution. The bone is then immersed in the second solution in the container, for further processing. The second solution to be drawn through the bone graft may include endotoxin-free deionized/distilled water, ethanolic solutions of water, or isotonic saline in endotoxin-free deionized/distilled water. During addition of the second solution to the container, the vacuum can be shut off until processing of the second solution through the bone is ready to resume.

The second solution is drawn through the bone in order to reduce the amount of the first solution in the bone graft and/or to deliver additional agents to be used in processing of the whole bone graft. For example, addition of ethanol (50% to 100%, vol to vol) to reduce bacterial, fungal and/or viral contaminants which might be present in the bone graft. The use of absolute (100%) ethanol in the second solution would further serve to dehydrate the bone, reducing subsequent times needed for freeze-drying.

Since the flow of solution through the bone graft will be less restricted during flushing with the second solution, the level of vacuum used (5 to 15 inches mercury vapor) is appropriately reduced to maintain an appropriate flow rate, preferably between 10 and 15 ml per minute.

The volume of the second solution which is drawn through the bone varies depending on the size of the bone being processed, the volume of the intermedullary canal of the bone being processed, and the concentration of detergent and/or ethanol used in the first solution, but in general should approximate a volume 10-fold greater than the volume of the bone graft being processed.

Following completion of flushing of the bone graft with the second solution, the bone graft may be removed from the container and processed into smaller bone grafts via procedures previously established for the production of such grafts.

B. Recirculation Method A: Using Positive and Negative Pressure to Move Solvent(s) Through an Essentially Intact Bone Graft and Associated Soft Tissue.

Following thawing under sterile conditions at room temperature, the bone is prepared for attachment of the solvent line by drilling a small hole approximately midway between the proximal and distal ends or by transecting the whole bone approximately midway between the proximal and distal ends. The bone is attached to the solvent source and placed into the solvent solution in a sterile cleaning container. This sterile cleaning container may be the "beaker" of a Branson ultrasonic cleaner, for example, Models 1210, 2210, 3210, etc. as size of the bone graft dictates, capable of operating at between 20 kHz and 50 kHz at temperatures up to 69±5° C. As solvent solution is forced through the bone graft, it is collected in a disposable container or recirculated.

The pressure source used to push the solvent solution through the bone graft will be sufficient to generate a flow of solution from a pressurized system, preferably a peristaltic pumping system (for example a Q2V piston size with a V200 Controller from FMI) approximating up to 2304 milliliters per minute. The use of peristaltic pumping systems facilitates retention of sterility in the solutions being induced to flow through the bone grafts. The actual pressure level or pumping rate is adjusted such that the flow rate of solution through the bone graft does not occur so rapidly that the bone marrow is not effectively solubilized, but rapidly enough to effectively remove solubilized bone marrow. Flow rates of solvent should range from 180 and 2,304 mls per minute with the preferred rates being in the range from 500 to 2,000 mls per minute, most preferably from 1,000 to 1,500 mls per minute.

The first solvent Bone Cleaning Solution or BCS to be drawn using a negative pressure flow or flushed using a positive pressure flow through the bone graft can consist of, for example, a sterile mixture of detergent and/or ethanol or other alcohol, in endotoxin-free deionized/distilled water. Detergents utilized include, but are not limited to, ionic and/or non-ionic detergents such as polyoxyethylene alcohols (Brij series, Lubrol W, etc.), polyethylene glycol p-isooctylphenylethers (Triton X series), Nonidet P-40, nonoxynol-9, polyoxyethylene nonylphenol (Triton N series, Surfonic N series, Igepal CO series), polyoxyethylene sorbitol esters (Tween series, Emasol series), the formulation known as ALLOWASH™ Solution (LifeNet Research Foundation, Virginia Beach, Va., pending patent application Ser. No. 08/620,856) in concentrations ranging between 0.001 weight percent to 2.0 weight percent with the preferred concentrations being in the range of 0.005 to 1.0 weight percent, most preferably from 0.01 to 0.5 weight percent. The concentration of alcohol which may be used in the first solution ranges from 5 to 95% (volume to volume) with the preferred range being from 10 to 30% (volume to volume). Suitable alcohols include but are not limited to: ethanol, isopropanol, butanol, n-propanol and methanol.

The second solvent to be drawn using a negative pressure flow or flushed using a positive pressure flow through the bone graft can include, for example, hydrogen peroxide in endotoxin-free deionized/distilled water (for example, from 1 to 5%, preferably 3% hydrogen peroxide), alcoholic solutions of water, or isotonic saline in endotoxin-free deionized/distilled water. The second solvent may be added to the container following removal of the first solution by simply pouring the second solvent into the container. During changes of the solution in the container, the solvent flow should be shut off in order to facilitate solvent changing in the container. The purpose of the second solvent is to reduce the amount of the first solvent in the bone graft and/or to deliver additional agents to be used in processing of the intact bone graft. For example, addition of hydrogen peroxide (3%), ethanol, or isopropyl alcohol (50% to 100%, vol to vol) to a washing solution serves to further reduce bacterial, fungal, and/or viral contaminants which might be present in the bone graft. The use of absolute (100%) ethanol or isopropyl alcohol or other alcohol further serves to dehydrate the bone, thereby reducing subsequent time needed for freeze-drying. Since the flow of solvent through the bone graft is less restricted during the flushing with the second, third, or subsequent solvent(s), the level of pressure used should be appropriately reduced to maintain an appropriate flow rate of 1,000 to 1,500 mls per minute. The volumes of the second, third, etc., solvents may vary depending on the concentration of detergent and/or alcohol used in the first solvent, but in general should approximate a volume 10 to 100-fold greater than the volume of the bone graft being processed.

Following completion of flushing of bone graft with the cleaning solvents, and washing solvents, the bone graft may be removed from the sterile container and processed into smaller bone grafts via procedures previously established for the production of such grafts or additional solvents may be flushed through the bone graft to add additional processing procedures/solutions into the total bone cleaning process.

Optional components may also be added to either the first, second, third, or subsequent solvents being used to clean and flush, respectively, the bone graft, including, but not limited to, antibiotics, antiviral agents (for example peroxide generating agents such as Exact™ a trademarked product marketed by ExOxEmis, Inc., San Antonio, Tex.), hydrogen peroxide, permeation enhancers (for example fatty acid esters such as laurate, myristate and stearate monoesters of polyethylene glycol), organic acids (for example citric acid) or dilute solutions of strong acids (for example hydrochloric acid).

(i) Recirculation Method A: In summary a. Initially about 200 to 1,000 mls, preferably about 400 to 600 mls and most preferably about 500 mls of a first solvent containing one or more detergents is drawn through the bone graft with associated soft tissue to waste using a negative pressure mediated flow of solvent at a temperature of from 37° C. to 44° C.

b. Thereafter the bone and soft tissue is flushed using a positive pressure mediated flow with a second solvent optionally containing a detergent (this second solvent may be the same or different from the first), where the second solvent is flushed to waste or recirculated through the bone. This flushing or recirculation is carried out for about 5 to 25 minutes, preferably about 10 to 20 minutes, and most preferably about 15 minutes, or until bone marrow removal is complete as indicated by absorbance of the effluent material at 410 nm. (Steps a and b may optionally be repeated using the same or a different solvent, if necessary, to facilitate further cleaning. The necessity for further cleaning, as well as the selection of the particular solvent, can be readily determined by one of ordinary skill in the art without undue experimentation, for example, by monitoring absorbance of the effluent material at 410 nm).

c. The second solvent is then removed from the bone graft and soft tissue by either: (a) flushing to waste using a positive pressure mediated flow with a third solvent, or (b)(i) drawing according to step a (about 500 mls) of a third solvent to waste using a negative pressure flow followed by (b)(ii) flushing using a positive pressure flow, a third solvent through the bone; where the third solvent preferably contains a decontaminating agent.

d. A fresh volume of the third solvent is then optionally recirculated using a positive pressure flow through the bone for a time period from about 5 to 25 minutes, preferably from about 10 to 20 minutes, and most preferably about 15 minutes.

e. Steps c and d are optionally repeated using new volumes of the same or different solvents. Preferably, steps c and d are repeated using a solvent containing one or more antibiotics and/or antivirals and/or antimycotics followed by removal of the antibiotics/antivirals/antimycotics, steps c and d may optionally be repeated using a solvent containing one or more alcohols, and finally repeated to remove the solvent containing alcohols, using sterile water as the solvent in steps c and d.

The order of use of solvents and the particular composition of a particular solvent used in the present process is not critical as long as the first solvent used is a solvent containing one or more detergents. The present process includes at least performing steps a and b using a first solvent containing one or more detergents.

C. Recirculation Method B: Using Negative Pressure to Pull Solvent Through a Bone Graft and Associated Soft Tissue Following thawing under sterile conditions at room temperature, the bone is prepared for attachment of the solvent line by drilling a small hole (preferably approximately midway between the proximal and distal ends of the bone) or by transecting the whole bone (preferably approximately midway between the proximal and distal ends of the bone). The bone is attached to the solvent source and placed into the solvent solution in a sterile cleaning container. This sterile cleaning container may be the "beaker" of a Branson ultrasonic cleaner, for example, Models 1210, 2210, 3120, etc., as size of the bone graft dictates, capable of operating at between 20 kHz and 50 kHz at temperatures up to 69±5° C. As solvent solution is pulled through the bone graft, it is collected in a disposable container or recirculated.

The pressure source used to pull solution through the bone grafts will be sufficient to generate a flow of solution from a system under negative pressure, preferably a peristaltic pumping system (for example a Q2V piston size with a V200 Controller from FMI) approximating up to 2304 milliliters per minute. The use of peristaltic pumping systems facilitates retention of sterility in the solutions being induced under negative pressure to flow through the bone graft. The actual pressure level or pumping rate is adjusted such that the flow rate of solution through the bone graft does not occur so rapidly that the bone marrow is not effectively solubilized, but rapidly enough to effectively remove solubilized bone marrow. Flow rates of solvent should range from 180 and 2,304 mls per minute with the preferred rates being in the range from 500 to 2,000 mls per minute, most preferably from 1,000 to 1,500 mls per minute.

The first solvent (Bone Cleaning Solution or BCS) to be pulled through the bone graft can consist of, for example, a sterile mixture of detergent and/or ethanol or other alcohol in endotoxin-free deionized/distilled water. Detergents utilized include, but are not restricted to, ionic and/or nonionic detergents such as polyoxyethylene alcohols (Brij series, Lubrol W, etc.), polyethylene glycol p-isooctylphenylethers (Triton X series), Nonidet P-40, nonoxynol-9, polyoxyethylene nonylphenol (Triton N series, Surfonic N series, Igepal CO series), polyoxyethylene sorbitol esters (Tween series, Emasol series), the formulation known as ALLOWASH™ Solution (LifeNet Research Foundation, Virginia Beach, Va., pending patent application Ser. No. 08/620,856) in concentrations ranging between 0.001 weight percent to 2.0 weight percent with the preferred concentrations being in the range of 0.005 to 1.0 weight percent, most preferably from 0.01 to 0.5 weight percent. The concentration of alcohol which may be used in the first solution ranges from 5 to 95% (volume to volume) with the preferred range being from 10 to 30% (volume to volume). Suitable alcohols include but are not limited to: methanol, ethanol, propanol, isopropanol, n-propanol, and/or butanol.

The second solvent to be drawn through the bone graft can include, for example, hydrogen peroxide in endotoxin-free deionized/distilled water (for example, from 1 to 5%, preferably 3% hydrogen peroxide), alcoholic solutions of water, or isotonic saline in endotoxin-free deionized/distilled water. The second solution may be added to the container following removal of the first solution by simply pouring the second solution into the container. During changes of the solution in the container, the solvent flow should be shut off in order to facilitate solvent changing in the container. The purpose of the second solution is to reduce the amount of the first solution in the bone graft and/or to deliver additional agents to be used in processing of the whole bone graft. For example, addition of hydrogen peroxide (3%), ethanol, or isopropyl alcohol (50% to 100%, volume to volume) to a washing solution would serve to further reduce bacterial, fungal, and/or viral contaminants which might be present in the bone graft. The use of absolute (100%) ethanol or isopropyl or other alcohol further serves to dehydrate the bone, thereby reducing subsequent time needed for freeze-drying. Since the negative pressure induced flow of solution through the bone graft is less restricted during the use of the second, third, or subsequent solvent(s), the level of pressure used should be appropriately adjusted to maintain an appropriate flow rate of 1,000 to 1,500 mls per minute. The volumes of the second, third, or subsequent solvent(s) may vary depending on the concentration of detergent and/or ethanol or other alcohol used in the first solution, but in general should approximate a volume 10 to 100-fold greater than the volume of the bone graft being processed.

Following completion of negative pressure mediated drawing of the bone graft with the cleaning and washing solvents, the bone graft may be removed from the sterile container and processed into smaller bone grafts via procedures previously established for the production of such grafts or additional solutions may be flushed through the bone graft to add additional processing procedures/solvents into the total bone cleaning process.

Optional components may also be added to either the first, second, third, or subsequent solvents being used including, but not limited to, antimycotics, antibiotics, antiviral agents (for example peroxide generating agents such as Exact™ a trademarked product marketed by ExOxEmis, Inc., San Antonio, Tex.), hydrogen peroxide, permeation enhancers (for example fatty acid esters such as laurate, myristate and stearate monoesters of polyethylene glycol), organic acids (for example citric acid) or dilute solutions of strong acids (for example, hydrochloric acid).

(i). Recirculation Method B: In summary a. Initially about 200 to 1,000 mls, preferably about 400 to 600 mls and most preferably about 500 mls of a first solvent containing one or more detergents is drawn through the bone graft to waste using a negative pressure mediated flow of solvent at 37° C. to 44° C.

b. Thereafter a second solvent which may be the same or different from the first is then: (a) drawn to waste or (b) recirculated through the bone using a negative pressure medicated flow of solvent. This drawing or recirculation is carried out for about 5 to 25 minutes, preferably about 10 to 20 minutes, and most preferably about 15 minutes, or until bone marrow removal is complete as indicated by absorbance of the effluent material at 410 nm. (Steps a and b may optionally be repeated using the same or a different solvent, if necessary, to facilitate further cleaning. The necessity for further cleaning, as well as the selection of the particular solvent, can be readily determined by one of ordinary skill in the art without undue experimentation, for example, by monitoring absorbance of the effluent material at 410 nm).

c. The second solvent is then removed from the bone graft by drawing a third solvent according to step a (about 500 mls) to waste using a negative pressure flow. The third solvent preferably contains a decontaminating agent.

d. A fresh volume of the third solvent is then optionally drawn or recirculated through the bone for a time period of from about 5 to 25 minutes, preferably from about 10 to 20 minutes, and most preferably about 15 minutes using a negative pressure redirected flow of solvent.

e. Steps c and d are optionally repeated using new volumes of the same or different solvents. Preferably, steps c and d are repeated using a solvent containing one or more antibiotics and/or antivirals and/or antimycotics followed by removal of the antibiotics/antivirals/antimycotics, steps c and d may optionally be repeated using a solvent containing one or more alcohols, and finally repeated to remove the solvent containing alcohols, using sterile water as the solvent in steps c and d.

The order of use of solvents and the particular composition of a particular solvent used in the present process is not critical as long as the first solvent used is a solvent containing one or more detergents. The present process includes at least performing steps a and b using a first solvent containing one or more detergents.

D. Sonication

An embodiment of the present invention involves a process for cleaning essentially intact bone grafts including attached soft tissue. First, bone materials procured from cadaveric donors are thawed. The bone is optionally debrided of external soft tissues. This debridement can include removal of excess cartilaginous tissues on the proximal and distal ends of bones at their points of articulation. The bone and attached associated soft tissue is attached to the vacuum source and placed into the solvent solution in an appropriate container, for example, a sterile basin or the tank of a commercially available ultrasonic cleaner, for example, Branson models 1210, 2210, 3210, 5210, or 8210, each of which hold essentially larger and larger volumes of cleaning solution. Preferably, the ultrasonic cleaner operates at (at) least 20 kHz, more preferably 30 kHz to 50 kHz, and most preferably 40 kHz to 47 kHz. The container is closed around the vacuum line or point of attachment to the bone graft to restrict movement of cleaning solution and a vacuum is applied to the system. The ultrasonic cleaner is then turned on with confirmation of cavitation performed. As solvent solution is drawn through the bone graft, it is collected in the disposable container. Solutions in the container can be changed by addition of new solution through a filling port. Co-pending application Ser. No. 08/646,520, filed May 7, 1996, entitled "A Recirculation Method for Cleaning Essentially Intact Bone Grafts Using Pressure Mediated Flow of Solvents and Bone Grafts Produced Thereby" is incorporated herein in its entirety and describes in detail methods for cleaning essentially intact bone grafts.

The vacuum source used to draw solution through the bone grafts will be between 15 and 35 inches Hg with the preferred range being between 20 and 30 inches Hg. The actual vacuum level is adjusted such that the flow rate of solution through the bone graft does not occur so rapidly that the bone marrow is not effectively solubilized, but rapidly enough to effectively remove solubilized bone marrow. Flow rates of solvent should range between 8 and 32 mls per minute with the preferred rates being between 15 and 25 mls per minute.

The first solvent to be drawn through the bone graft will consist of a sterile mixture of detergent and/or alcohol, for example, ethanol or isopropanol in endotoxin-free deionized/distilled water. Detergents utilized may include, but not be restricted to, ionic and/or nonionic detergents such as polyoxyethylene alcohols (Brij series, Lubrol W, etc.), polyethylene glycol p-isooctylphenylethers (Triton X series), Nonidet P40/Igepal CA 630, Nonoxynol-9 Igepal CO 630, polyoxyethylene nonylphenol (Triton N series, Surfonic N series, Igepal CO series), polyoxyethylene sorbitol esters (Tween series, Emasol series), the formulation known as ALLOWASH™ Solution (LifeNet Research Foundation, Virginia Beach, Va.) in concentrations ranging between 0.001 wt % to 2 wt % with the preferred concentrations being between 0.01 wt % and 0.5 wt %. The concentration of alcohol which may be used in the first solution ranges between 5% and 95% (volume to volume) with the preferred range being between 10% and 30% (volume to volume).

The second solvent to be drawn through the bone graft will consist of endotoxin-free deionized/distilled water, alcoholic solutions of water, or isotonic saline in endotoxin-free deionized/distilled water. The second solution may be added to the container, used to contain the first solution, using the filling port. During addition of the second solvent to the container, the vacuum should be shut off in order to facilitate filling of the container. Ultrasonic cleaning may be used during this second solvent process, however it is generally not necessary since the first solvent processing is maximally effective in facilitating removal of bone marrow and bone marrow elements. The purpose of the second solvent is to reduce the amount of the first solution in the bone graft and/or to deliver additional agents to be used in processing of the essentially intact bone graft. For example, addition of ethanol or isopropanol (50% to 100%, volume to volume) to the washing solvent would serve to reduce bacterial, fungal, and/or viral contaminants which might be present in the bone graft. The use of absolute (100%) ethanol in the second solution would further serve to dehydrate the bone, reducing subsequent times needed for freeze-drying. Since the flow of solvent through the bone graft will be less restricted during the flushing with the second solvent, the level of vacuum used should be appropriately reduced to maintain an appropriate flow rate between 10 and 15 ml per minute. The volume of the second solvent may vary depending on the concentration of detergent and/or ethanol used in the first solvent, but in general should approximate a volume 10-fold greater than the volume of the bone graft being processed.

Following completion of flushing of bone graft with the second solution, the bone graft may be removed from the sterile container and optionally processed into smaller bone grafts via procedures previously established for the production of such grafts.

Optional components may also be added to either the first or second solvent being used to clean and flush, respectively, the bone graft, including but not limited to, antibiotics, antiviral agents (for example, peroxide generating agents such as Exact (a trademarked product marketed by ExOxEmis, Inc., San Antonio, Tex.)), hydrogen peroxide, permeation enhancers (for example, fatty acid esters such as laurate, myristate and stearate monoesters of polyethylene glycol), organic acids (for example, citric acid) or dilute solutions of strong acids (for example, hydrochloric acid).

Soft tissue not attached to bone can also be processed as above without the use of a pressure mediated flow of solution.

E. Preferred Method for Cleaning of Non-Bone Tissues.

The soft tissue graft is cleansed using a pulsatile water apparatus making sure to remove as much of the marrow elements and blood deposits as possible. Preferably soft tissue grafts attached to bone are then placed in a sterile can entirely filled with sterile water (approximately 3 liters of sterile water) at 27° C. to 44° C., preferably 40° C. Alternatively, the present cleaning solution can be used in place of sterile water or an additional agitation can be preformed using the present cleaning solution after agitation using water. Both Achilles tendons and patellar ligaments from the same donor may be placed in the same can.

The can is then agitated for 10–12 minutes at 450–550 rpms preferably for at least 12 minutes at 500 rpm's. The graft is then visually inspected and if is not cleaned sufficiently, it is again cleaned using for example pulsatile lavage, followed by further cleaning using vigorous agitation. Such determination can be readily made by one of ordinary skill in the art to which the present invention pertains.

For soft tissue grafts attached to bone and soft tissue grafts not attached to bone, the graft is then placed in a basin containing a 1:100 dilution of the present composition (Bone Cleaning Solution (BCS)) or other surfactant(s) for at least 15 minutes, preferably 15 minutes. The tissue can be incubated by soaking, sonicating or agitation, optionally in a negative pressure environment at a pressure from about 20 to 30 inches of mercury vapor, preferably by soaking at atmospheric pressure. The graft is then rinsed at least three times, preferably 3 times with sterile water to remove any residual surfactants. The sterile rinse water which accumulates in the "rinse" basin is then discarded.

The entire fashioned graft is then placed in a small basin containing one or more decontaminating agents, preferably U.S.P. grade 70% isopropyl alcohol for 2–5 minutes. The graft is then placed in a sterile basin containing an antibiotic solution. The fashioned graft remains in this solution for at least 15 minutes, preferably 15 minutes. The graft should not be left in the isopropyl alcohol for more than 5 minutes, as this will tend to desiccate the soft tissue.

The graft is then thoroughly soaked by immersing each deposit into a sterile water bath for a minimum of five minutes, preferably 15 minutes, to remove any remaining reagents. Using the pulsative water apparatus, any remaining marrow elements and/or blood deposits are removed from the bone and/or soft tissue. If the graft(s) are to be freeze dried they are placed on sterile fine mesh gauze. The gauze is trimmed just beyond the edges of the graft.

The graft(s) are then measured, assigned identification numbers, and packaged as appropriate.

(i) Summary of Soft Tissue Cleaning Protocols:

Associated soft tissue is cleaned according to the present invention as follows:

a. The graft is incubated in one or more of the present bone cleaning solutions with the incubation including one or more of immersion, soaking, agitation (e.g., gyratory shaker or paint can shaker) and sonication optionally in a negative pressure environment, to produce a bone cleaning solution cleaned graft;

b. the bone cleaning solution cleaned graft is then rinsed with water optionally including one or more decontaminating agents to produce a rinsed graft;

c. the rinsed graft is incubated in one or more decontaminating agents with the incubation including one or more of immersion, soaking, agitation (e.g., gyratory shaker or paint can shaker) and sonication optionally in a negative pressure environment, to produce a decontaminated graft; and d. the decontaminated graft is incubated in water optionally including one or more decontaminating agents, optionally in a negative pressure environment, to produce a cleaned graft suitable for transplantation into a human.

Prior to step (a), the graft may optionally be subjected to:

pre-cleaning with water optionally including one or more of the present bone cleaning solutions, pre-cleaning including cleaning by one or more of pulsatile lavage, soaking, immersion, agitation and sonication, optionally in a negative pressure environment, to produce a pre-cleaned graft, and agitating said pre-cleaned graft in water optionally including one or more of the present bone cleaning solutions, agitating including agitation achieved by using a gyratory shaker or a paint can shaker, optionally carried out in a negative pressure environment.

After step (c) and prior to step (d) the graft may optionally be incubated in one or more decontaminating agents including one or more antibiotics, incubation including one or more of immersion, soaking, agitation (e.g., gyratory shaker or paint can shaker) and sonication optionally carried out in a negative pressure environment, to produce an antibiotic cleaned graft.

EXAMPLES

The following illustrative examples describe the instant invention in more detail. However, they are not intended to limit the scope of the specification and claims.

Example I

A femur was thawed, debrided of excess soft tissue (including the excess cartilage present on the articulating surfaces) and a hole approximately ¼ to ⅝ inch outside diameter was drilled in the bone shaft approximately midway between the distal and proximal ends of the bone. The hole was only drilled deep enough to penetrate the cortical bone so that intramedullary bone marrow could be flushed from the bone and so a tapping port could be securely inserted into the hole. The vacuum line was attached securely to the tapping port.

Two liters of a solution of 10% ethanol in a 0.01× solution containing 0.0066 weight percent Brij-35, 0.002 weight percent Nonidet P-40, and 0.002 weight percent Nonoxynol-9 in endotoxin free water were added to an open container in a clean room environment under sterile conditions. The femur having the vacuum line attached via the tapping port was then placed into the container, and immersed towards the bottom of the container.

The temperature of the cleaning solution was adjusted to 45° C. prior to addition of the bone graft. A vacuum was applied to the system and maintained in the range of 25 to 27 inches Hg vapor. The flow rate of solution through the bone graft was maintained at approximately 10 ml per minute by adjusting the vacuum. The solution collected in the disposable container was dark red initially, turning to a color similar to that of serum as bone marrow was removed from the graft. By sampling the effluent material being removed from the bone graft, via a sampling port accessible by use of a syringe, it was possible to monitor completion of bone marrow removal by measuring absorbance at 410 nm, to determine when essentially all of the bone marrow was removed from the bone graft. After drawing two liters of first solution through the bone graft, the vacuum to the system was discontinued and the open container was refilled with one liter of endotoxin-free deionized/distilled water. The vacuum was reapplied to the system. The deionized/distilled water was flushed through the bone graft at approximately 15 ml per minute to remove the detergent solution. Following the flushing of detergent solution from the bone graft, vacuum was discontinued to the system and the bone graft was removed from the open container, after which the vacuum line and tapping port were removed. The bone graft was then ready for further processing into small bone grafts as required.

Example II

A femur was thawed, prepared and cleaned in the same manner as indicated in Example I, with the following exceptions. The bone was cut in half using a bone saw. The proximal end of the femur was used in this example, however, the distal end of the femur would be similarly processed. Pulsavac lavage was applied to remove bone marrow from the luminal space. One liter of solution of 10% ethanol in a 0.01× solution container 0.0066 weight percent Brij-35 (0.55 mM), 0.002 weight percent Nonidet P-40 (0.33 mM), and 0.002 weight percent Nonoxynol-9 (0.32 mM) in endotoxin free water was added. A sealing cap was placed over the cut end of the bone graft and secured using a clamping device. A vacuum line was attached securely to an access line in the sealing cap.

The bone graft having the vacuum line attached via the sealing cap and access line was then placed into the container, and immersed towards the bottom of the container. The temperature of the cleaning solution was adjusted to room temperature (approximately 27° C.) prior to addition of the bone graft. Vacuum was applied to the system and maintained in the range of about 25 to 27 inches Hg vapor. The flow rate of solution through the bone graft was maintained in the range of about 25 to 27 inches Hg vapor. The flow rate of solution through the bone graft was maintained at approximately 10 ml per minute by adjusting the vacuum.

The solution collected in the disposable container was initially dark red, and turned to a color similar to that of serum as bone marrow was removed from the graft. By sampling the effluent material being removed from the bone graft, via a sampling port accessible by use of a syringe, it was possible to monitor completion of bone marrow removal by monitoring absorbance at 410 nm, and it was possible to determine when essentially all of the bone marrow was removed from the bone graft.

After drawing one liter of first solution through the bone graft, the vacuum to the system was discontinued and the open container was refilled with one liter of endotoxin-free deionized/distilled water (second solution), after which vacuum was reapplied to the system. the deionized/distilled water was flushed through the bone graft at approximately 15 ml per minute to remove the detergent solution. Following the flushing of detergent solution from the bone graft, vacuum was discontinued to the system and the bone graft was removed from the container. Next, the sealing cap and vacuum line were removed. The bone graft was then ready for further processing into small bone grafts as required.

Example III

Achilles Tendon

Using a band or Stryker saw, jagged edges were cut from a calcaneus bone block left from the recovery procedure. The bone block was at least 2.0 cm long (proximal to distal measurement). Any large amounts of muscle were removed from the tendon material. Leaving as much soft tissue as possible on the graft initially protects the tendon during the shaking phase. This prevents the calcaneus from disrupting the tendon fibers during agitation.

The Achilles tendon graft was cleansed using a pulsatile water apparatus making sure to remove as much of the marrow elements as possible. The graft was then placed in a sterile can entirely filled with sterile water (approximately 3 liters of sterile water) at 40° C. The can was then placed in a sterile polyethylene bag and agitated for 12 minutes at 500 rpm's. The graft was then visually inspected.

The sterile water was then decanted and any remaining gastrocnemius muscle and fat from the superior aspect of the graft was removed with care being taken not to remove any of the tendon itself The graft was then placed in a basin containing a 1:100 dilution of ALLOWASH™ solution. The graft was then rinsed three times with sterile water to remove any residual surfactants. The sterile rinse water which accumulated in the "rinse" basin was then discarded.

The entire fashioned graft was then placed in a small basin containing U.S.P. grade 70% isopropyl alcohol for 5 minutes. The graft was then placed in a sterile basin containing an antibiotic solution. The fashioned graft remained in this solution for 15 minutes.

The graft was then thoroughly soaked by immersing into a sterile water bath for 15 minutes, to remove any remaining reagents. Using the pulsative water apparatus, any remaining marrow elements were removed from the bone. The graft was placed on sterile fine mesh gauze. The gauze was trimmed just beyond the edges of the graft.

The length of the graft was measured to the nearest tenth of a centimeter. The graft was assigned identification numbers.

The graft and gauze were rolled into a tube and together placed into a 250 ml glass bottle and labeled as appropriate.

TABLE I

Achilles Tendon

| Treatment | Tensile Force (N) | Strain (in/in) | Tensile Strength (MPa) | Youngs Modulus (MPa) |
|---|---|---|---|---|
| BCS | 318.9 | 0.45 | 8.828 | 59.332 |
| BCS | 988.395 | 0.51 | 1.895 | 11.487 |
| BCS | 375.43 | 0.59 | 4.773 | 27.849 |
| BCS | 1133.407 | 0.64 | 2.857 | 20.083 |
| BCS | 614.744 | 0.5 | 0.439 | 2.825 |
| NBCS | 498.646 | 0.27 | 8.874 | 70.873 |
| NBCS | 937.685 | 0.62 | 4.607 | 9.724 |
| NBCS | 897.651 | 0.44 | 3.938 | 9.515 |
| NBCS | 1293.988 | 0.64 | 0.327 | 6.811 |
| NBCS | 853.169 | 0.39 | 0.609 | 7.827 |
| Average BCS | 686.18 | 0.54 | 3.7584 | 24.315 |
| SD | 363.29 | | | |
| Max/Min | 1133/319 | | | |
| Range | 814.51 | | | |
| Average NBCS | 896.23 | 0.47 | 3.671 | 20.950 |
| SD | 282.78 | | | |
| Max/Min | 1294/499 | | | |
| Range | 795.34 | | | |

BCS = Bone Cleaning Solution (0.01X ALLOWASH Solution)
MPa = MegaPascals
NBCS = No Bone Cleaning Solution (Endotoxin-Free Deionized/Distilled Water)
(N) = Newtons
Strain units are dimensionless

Example IV
Patellar Ligament

The patella with patellar ligament intact was removed from the tibia by fashioning a section of bone from the tibial tuberosity with a band saw or Stryker saw. This bone block was at least 2.8 cm long (2.8 cm distal to the patellar ligament insertion site), at least 2.0 cm wide, and at least 1.2 cm thick (anterior-posterior measurement). Both the medial and lateral sides of the patella were trimmed to expose the marrow. Any large amount of muscle was removed from the tendon material. Note that leaving soft tissue on the graft initially protects the tendon during the shaking phase. This soft tissue prevents the patella and tibia bone blocks from later disrupting the tendon fibers during agitation.

The patellar ligament was cleansed using a pulsatile water apparatus making sure to remove as much of the marrow elements as possible. The graft was then placed in a sterile can entirely filled with sterile water at 40° C. This required approximately 3 liters of sterile water. Note that both achilles tendons and patellar ligaments may be placed in the same shaker can. However, achilles tendons and patellar ligaments should not be placed with other cut grafts from the same donor in that other cut grafts can cut and tear soft tissue grafts. The can was then placed in a sterile polyethylene bag and agitated for 12 minutes at 500 rpms.

After decanting the sterile water solution from the can, all extraneous soft tissue, including retinaculum, were carefully removed using sharp and blunt dissection techniques. Care was taken not to cut the ligament fibers during dissection.

The patellar ligament was greater than 2.5 cm at the tibial insertion site. Accordingly, the patella, ligament, and tibial bone block were carefully bisected using the band saw. Each bisected ligament had a tendon width of at least 1.2 cm. (Note: if the ligament at the insertion site is less than 2.5 cm, the patella, ligament, and tibial bone block should not be bisected.) The tibial tuberosity bone block was trimmed to yield a rectangular appearing section, at least 1.2 cm wide, 2.8 cm long, and 1.2 cm thick Anterior-Posterior (A-P). The fashioned tibial tuberosity bone block should be the same width as the ligament at the insertion site (at least 1.2 cm).

The graft was then placed in a basin containing a 1:100 dilution of ALLOWASH™ solution for 15 minutes. The graft was placed into an empty basin and rinsed three times with copious amounts of sterile water to remove any residual bone cleaning solution. Any sterile water which accumulated in the basin was discarded.

The entire fashioned graft was placed in a small basin containing U.S.P. grade 70% isopropyl alcohol for 5 minutes. The graft should not be left in the isopropyl alcohol for more than 5 minutes, as this desiccates the tissue. The graft was then placed in a sterile basin containing an antibiotic solution for 15 minutes. The graft was then soaked thoroughly by immersing the deposit into a sterile water bath for 5 minutes to remove any remaining reagents. Pulsatile lavage was then used to remove any remaining marrow elements from the bone. The fashioned graft was then placed on sterile fine mesh gauze and the gauze was trimmed to just beyond the edges of the graft.

The bisected graft was placed on sterile fine mesh gauze, the gauze was trimmed to just beyond the edges of the graft and the graft/gauze combination was placed into a 250 ml bottle.

(Note: If the fashioned graft(s) are to be frozen, the fashioned graft is cultured for bacterial contamination. One cotton-tipped applicator is placed into a thiogylocolate broth tube and one into a trypticase-soy broth tube. The graft material is then ready for packaging/wrapping and placement in either the freeze dryer or appropriate freezer.)

TABLE II

Patellar Ligament

Strength Data
Units: kiloPascals unless noted

| Donor ID | Tensile Strength BCS | Tensile Force (N) BCS | Strain Rate (In/In) BCS | Tensile Strength NBCS | Tensile Force (N) NBCS | Strain Rate (In/In) NBCS |
|---|---|---|---|---|---|---|
| 95-1119 | 7636 | 2290 | 0.46 | 6971 | 2415 | 0.38 |
| 96-0162 | 5791 | 2241 | 0.55 | 9393 | 2994 | 0.53 |
| 96-0187 | 2537 | 972 | 0.42 | 3890 | 1315 | 0.45 |
| 96-0190 | 8081 | 2059 | 0.52 | 7054 | 1966 | 0.5 |
| 96-0204 | 6676 | 1903 | 0.46 | 6544 | 1992 | 0.56 |
| 96-0212 | 3189 | 862 | 0.41 | 1807 | 524 | 0.58 |
| 96-0269 | 4796 | 1748 | 0.55 | 6700 | 2460 | 0.39 |
| 96-0300 | 5802 | 2055 | 0.64 | 5737 | 2139 | 0.52 |
| 96-0565 | 7207 | 1953 | 0.53 | 7206 | 3674 | 0.49 |
| 96-0591 | 6024 | 2002 | 0.53 | 6431 | 2099 | 0.51 |
| 96-0619 | 7858 | 2793 | 0.46 | 7251 | 2709 | 0.45 |
| 8409-10135 | 9077 | 2922 | 0.47 | 8734 | 3251 | 0.45 |
| Average | 6222.83 | 1983.33 | 0.50 | 5476.50 | 2294.83 | 0.48 |
| SD | 1969.594 | 606.873 | 0.065 | 2009.296 | 846.213 | 0.062 |
| Max/Min | — | 2922/972 | — | — | 3674/524 | — |
| Range | — | 1950 | — | — | 3150 | — |

Example V

*Fascia lata*

Any remaining muscle tissue was first removed from the *fascia lata*. The *fascia lata* was then placed with the subcutaneous layer uppermost, on a clean, blue drape towel. Using blunt dissection techniques, all of the fat and extraneous soft tissue was removed from the graft material. The graft was kept moist with isotonic antibiotic solution to prevent desiccation during processing. Any torn fibers were removed from the edges of the graft material, creating a graft of rectangular shape. Care should be taken to obtain the largest graft possible. (Note that this procedure can process a single graft or multiple grafts.)

The graft was then placed in a basin containing a 1:100 dilution of ALLOWASH™ solution for 15 minutes. The graft was then placed into an empty basin and rinsed three times with sterile water to remove any residual surfactant. Any sterile water which accumulated in the basin was discarded.

The fashioned graft was then placed in a basin containing 70% isopropyl alcohol for 5 minutes. Exposure of the graft to alcohol for more than 5 minutes is avoided, to reduce desiccation of the tissue. The graft was then placed in a basin containing an antibiotic solution for 15 minutes.

The graft was then thoroughly soaked by immersion in a sterile water bath for 5 minutes, to remove any remaining reagents. Thereafter, the fashioned graft was placed on sterile fine mesh gauze, and the gauze was trimmed to just beyond the edges of the graft. The width and length of the graft(s) were then measured to the nearest tenth of a centimeter.

The graft(s) and gauze were rolled into tubes and placed into a 250 ml glass bottle. In operations were multiple grafts are processed, this step is repeated until all grafts are bottled.

If the *fascia lata* is to be preserved in U.S.P. grade 0.9% sodium chloride for irrigation, the measured deposit is placed into a sterile 120 ml bottle. Approximately 60 ml of U.S.P. grade 0.9% sodium chloride for irrigation is poured into the bottle and the deposit is covered. A stopper is placed in the bottle and pressed tightly to prevent the saline from leaking. These steps were repeated for each representative sample deposit.

Then the *fascia lata* deposit(s) and representative sample pieces are wrapped according to the procedure for wrapping freeze dried tissue and transported to the freeze dryer room. The deposits are placed in a disinfected freeze dryer, the stopper is loosened, and a vacuum in the dryer is drawn.

TABLE III

Fascia Lata

| Donor ID | Tensile Force (N) BCS | Strain (In/In) BCS | Tensile Force (N) NBCS | Strain (In/In) NBCS |
|---|---|---|---|---|
| 96-0162 | 298 | 0.54 | 291 | 0.47 |
| 96-0162 | 405 | 0.59 | 387 | 0.61 |
| 96-0162 | 170 | 0.64 | 576 | 0.62 |
| 96-0162 | 177 | 0.4 | 347 | 0.54 |
| 96-0187 | 210 | 0.42 | 141 | 0.36 |
| 96-0187 | 211 | 0.37 | 171 | 0.5 |
| 96-0187 | 175 | 0.31 | — | — |
| 96-0187 | 147 | 0.31 | 168 | 0.33 |
| 96-0190 | 211 | 0.4 | 467 | 0.24 |
| 96-0190 | 229 | 0.42 | 481 | 0.24 |
| 96-0190 | 156 | 0.31 | 253 | 0.17 |
| 96-0190 | 164 | 0.22 | 317 | 0.22 |
| 96-0212 | 207 | 0.53 | 328 | 0.53 |
| 96-0212 | 456 | 0.5 | 304 | 0.49 |
| 96-0212 | 140 | 0.42 | 369 | 0.41 |
| 96-0212 | 265 | 0.39 | 375 | 0.49 |
| 96-0269 | 244 | 0.24 | 355 | 0.43 |
| 96-0269 | 283 | 0.23 | 407 | 0.37 |
| 96-0269 | 205 | 0.19 | — | — |
| 96-0269 | — | — | 325 | 0.26 |
| 96-0304 | 283 | 0.47 | 222 | 0.46 |
| 96-0304 | 129 | 0.37 | 212 | 0.3 |
| 96-0304 | 159 | 0.49 | 199 | 0.4 |
| 96-0304 | 194 | 0.44 | 159 | 0.27 |
| 95-1415 | 347 | 0.43 | 422 | 0.68 |
| 95-1415 | 262 | 0.57 | 363 | 0.37 |
| 95-1415 | 412 | 0.44 | 355 | 0.49 |
| 95-1415 | 431 | 0.48 | 335 | 0.45 |
| 96-1525 | — | — | 434 | 0.34 |
| 96-1525 | 182 | 0.29 | 564 | 0.35 |
| 96-1525 | 114 | 0.23 | 237 | 0.31 |
| 96-1525 | — | 0.23 | 326 | 0.23 |
| AVERAGE | 236.759 | 0.395 | 329.667 | 0.398 |
| SD | 94.322 | 0.120 | 112.606 | 0.130 |

TABLE III-continued

Fascia Lata

| Donor ID | Tensile Force (N) BCS | Strain (In/In) BCS | Tensile Force (N) NBCS | Strain (In/In) NBCS |
|---|---|---|---|---|
| Max/Min | 456/114 | — | 576/141 | — |
| Range | 342 | — | 435 | — |

BCS = Bone Cleaning Solution (0.01X Allowash Solution)
NBCS = No Bone Cleaning Solution
— = no data available
(N) - Newtons

Results

No significant differences were observed in the tensile strength of untreated Achilles tendons as compared to tendons treated with a bone cleaning solution of the present invention. No significant differences were observed in the tensile strength of *fascia lata* treated with bone cleaning solution when compared with untreated *fascia lata*.

The tensile strength of patellar ligaments was tested. No significant differences were observed between bone cleaning solution treated grafts and untreated grafts.

The tensile strength of *fascia lata* was tested. No significant differences were observed between bone cleaning solution treated grafts and untreated grafts.

The Young's modulus of untreated Achilles tendons and Achilles tendons treated with bone cleaning solution was measured. No significant differences were observed between bone cleaning solution treated grafts and untreated grafts.

The Young's modulus of untreated patellar ligaments and patellar ligaments treated with bone cleaning solution was measured. No significant differences were observed between bone cleaning solution treated grafts and untreated grafts.

The Young's modulus of untreated *fascia lata* of males and female and *fascia lata* of males and female with bone cleaning solution was measured. No significant differences were observed between bone cleaning solution treated grafts and untreated grafts.

The type and frequency of patellar ligament failures after treatment with a present bone cleaning solution and without treatment with a present bone cleaning solution were found to be as follows in Table V:

TABLE IV

| Failure | ALLOWASH ™ | No ALLOWASH ™ |
|---|---|---|
| Cracked Bone | 4 | 5 |
| Tear at Bone | 9 | 6 |
| Tissue Tear | 2 | 0 |
| Other | 0 | 3 |

TABLE V

Young's Modulus Data (Tensile Strength)
Units: kiloPascals

| | AVERAGES | |
|---|---|---|
| Donor ID | BCS Treated | NBCS Treated |
| 95-1119 | 44713 | 34081 |
| 96-0162 | 34385 | 23044 |
| 96-0187 | 15369 | 28065 |
| 96-0190 | 41091 | 35590 |
| 96-0204 | 27552 | 12206 |
| 96-0212 | 18413 | 16501 |
| 96-0269 | 24730 | 55904 |
| 96-0300 | 29238 | 25605 |
| 96-0565 | 57603 | 67653 |
| 96-0591 | 26933 | 44974 |
| 96-0619 | 44787 | 37912 |
| B409-10135 | 61179 | 35515 |
| GRAND AVERAGE | 35499.42 | 34754.17 |

BCS = Bone Cleaning Solution (0.01X Allowash Solution)
NBCS = No Bone Cleaning Solution

Example VI

Viral Inactivation Data for the Soft Tissue Treatment by ALLOWASH™ Solution.

This experiment tested the antiviral effect of ALLOWASH™ Solution against HIV-1/LA1 in 3 day PHA stimulated PBM cells from the Red Cross. RTU media contained HR-IL2 (26.5 Units/ml). Virus was incubated with varying amounts of ALLOWASH™ solution for 5 minutes at room temperature. This experiment was performed in a 24 well plate 4×10(5) cells/ml. One ml of supernatant was spun at 12,000 rpm for 2 hours at 4° C. using the Jouan MR 1822. 10 ml of resuspended sample of RT'd using 75 ml of 4×3H-TTP cocktail. A semi-automated RT was performed on disrupted pellets using the Packard harvester and direct beta counter. All CPM values are averages of duplicate RT's.

The results indicated that at less than 0.0025× Allowash solution (cleaning is generally performed using a concentration of 0.01× at 0.01 times) 100% of the HIV was inactivated within 5 minutes at room temperature.

TABLE VI

| Treatment | Concn. | CPM | CMP/ml | % Inhibition Comments (corrected) |
|---|---|---|---|---|
| Blanks | | 40 | | |
| | | 82 | | |
| Average | | 61 | | |
| Stdev | | 30 | | |
| HIV Std. | | 1,591 | 18,910 | |
| Virus Titration | 2.5 µl | 789 | 7,890 | |
| Average | | 1,049 | 10,490 | |
| Stdev | | 919 | 9,190 | |
| | 10 µl | 1,402 | 14,020 | |
| | | 1,677 | 16,770 | |
| Average | | 1,540 | 15,400 | |
| Stdev | | 194 | 1,945 | |
| UI Controls | | 240 | 2,400 | |
| | | 364 | 3,640 | |
| | | 196 | 1,960 | |
| Average | | 224 | 2,235 | |
| Stdev | | 112 | 1,119 | |
| inf. Control | | 963 | 9,630 | |
| HIV-1/LA1 | | 1,134 | 11,340 | |
| P-89, 4.17–5.01 | | 1,168 | 11,680 | |
| from PMB cells | | 1,957 | 19,570 | |
| 5 µl of virus/well | | | | |
| Average | | 1,306 | 13,060 | 0.0 |
| Stdev | | 444 | 4,436 | |
| Virus 5 µl+ | 0.025X | 109 | 1,090 | 110.6 EC$_{50}$ = <0.025X |
| 10X Allowash | | 230 | 2,300 | 99.4 |
| 5 µl | | 194 | 1,940 | 102.7 |
| | | 65 | 650 | 114.6 |

TABLE VI-continued

| Treatment | Concn. | CPM | CMP/ml | % Inhibition Comments (corrected) |
|---|---|---|---|---|
| Average | | 150 | 1,495 | 106.5 |
| Stdev | | 76 | 758 | 105.5 |
| Virus 5 µl+ | 0.0125X | 102 | 1,020 | 111.2 $EC_{50} = 0.0125X$ |
| 10X Allowash | | 94 | 940 | 112.0 |
| 5 µl | | 211 | 2,110 | 101.2 |
| | | 238 | 2,380 | 98.7 |
| Average | | 161 | 1,610 | 105.8 |
| Stdev | | 74 | 740 | |
| Virus 5 µl+ | 0.0025X | 215 | 2,150 | 100.8 $EC_{50} = <0.0025X$ |
| 1X Allowash 5 µl | | 83 | 830 | 113.0 |
| | | 80 | 800 | 113.2 |
| | | 92 | 920 | 112.2 |
| Average | | 118 | 1,175 | 109.8 |
| Stdev | | 65 | 652 | |

Although the invention has been described with reference to particular means, materials and embodiments, it is to be understood that the invention is not limited to the particulars disclosed and extends to all equivalents within the scope of the claims.

All the references cited above are incorporated herein in their entirety by reference.

What is claimed is:

1. A method for producing a soft tissue graft suitable for transplantation into a human, comprising:
    sonicating said soft tissue with a solvent comprising one or more detergents in an ultrasonic cleaner at a temperature and for a time period effective to produce cleaned soft tissue essentially free from blood deposits.

2. A soft tissue graft suitable for transplantation into a human, comprising the cleaned soft tissue produced by the process as claimed in claim 1.

3. The soft tissue graft of claim 2, wherein said associated soft tissue comprises one or more members selected from the group consisting of ligament tissue, tendon tissue, periosteum, cartilage, menisci and *fascia lata* tissue.

4. A soft tissue graft produced by the process as claimed in claim 1, wherein said graft is essentially free from bacterial, viral and fungal contamination.

5. A method for producing a soft tissue graft including attached to an essentially intact bone suitable for transplantation into a human, comprising:
    inducing a negative pressure mediated flow of a first solvent, said first solvent comprising one or more detergents, through an opening in a bone shaft of said essentially intact bone graft and associated soft tissue to produce a cleaned intact bone graft including associated soft tissue;
    sonicating said essentially intact bone graft and associated soft tissue in a container with said first solvent using an ultrasonic cleaner,
    wherein said inducing and said sonicating are carried out simultaneously for a time effective to produce a cleaned intact bone graft and associated soft tissues essentially free from bone marrow.

6. A soft tissue graft produced by the process as claimed in claim 5, wherein said graft is essentially free from bacterial, viral and fungal contamination.

7. A method for producing a soft tissue graft optionally attached to bone suitable for transplantation into a human, comprising:
    sonicating said soft tissue using an ultrasonic cleaning device with a first solvent comprising one or more detergents to produce a first cleaned soft tissue graft, and wherein said first cleaned soft tissue is essentially free from blood deposits.

8. The method of claim 7, further comprising:
    sonicating said first cleaned soft tissue graft using an ultrasonic cleaning device with a second solvent comprising one or more members selected from the group consisting of: an antibiotic, an antimycotic and an antiviral agent, to produce a second cleaned soft tissue graft; and
    sonicating said second cleaned soft tissue graft using an ultrasonic cleaning device with a third solvent comprising one or more decontaminating agents to produce a third cleaned soft tissue graft.

9. The method of claim 8, further comprising:
    sonicating said second cleaned soft tissue graft with sterile water prior to sonication with said third solvent.

10. The method of any one of claims 8 or 9, further comprising:
    sonicating said third cleaned soft tissue graft with a fourth solvent comprising one or more alcohols to produce a fourth cleaned soft tissue graft.

11. The method of claim 10, further comprising:
    washing said fourth cleaned soft tissue graft and with sterile water.

12. The method of claim 7, further comprising:
    agitating said first cleaned soft tissue graft with a second solvent comprising one or more members selected from the group consisting of: an antibiotic, an antimycotic and an antiviral agent, to produce a second cleaned soft tissue graft; and
    agitating said second cleaned soft tissue graft with a third solvent comprising one or more decontaminating agents to produce a third cleaned soft tissue graft.

13. The method of claim 12, further comprising:
    agitating said second cleaned soft tissue graft with sterile water prior to sonication with said third solvent.

14. The method of claims 12 or 13 further comprising:
    agitating said third cleaned soft tissue graft with a fourth solvent comprising one or more alcohols to produce a fourth cleaned soft tissue graft.

15. The method of claim 14, further comprising washing said fourth cleaned soft tissue graft with sterile water.

16. The method of claim 15, wherein said washing comprises one or more of soaking, sonicating, lavage and agitation.

17. The method of claim 16, wherein said washing is conducted in a negative pressure environment.

18. The method of any one of claims 1, or 7, wherein said soft tissue graft comprises one or more members selected from the group consisting of ligament tissue, tendon tissue, periosteum, cartilage, menisci and *fascia lata* tissue.

19. A soft tissue graft produced by the process as claimed in claim 7, wherein said graft is essentially free from bacterial, viral and fungal contamination.

20. A method for producing a soft tissue graft suitable for transplantation into a human, comprising:
    sonicating said soft tissue in one or more bone cleaning compositions to produce a cleaned graft;
    incubating said cleaned graft in one or more decontaminating agents to produce a decontaminated graft; and
    incubating said decontaminated graft in water to produce soft tissue graft suitable for transplantation into a human.

21. A soft tissue graft produced by the process as claimed in claim 20, wherein said graft is essentially free from bacterial, viral and fungal contamination.

22. The method of claim 20, wherein said incubating comprises one or more or soaking, sonicating, lavage and agitation.

23. The method of claim 22, wherein said washing is conducted in a negative pressure environment.

24. The method of any one of claims 20 or 22, wherein said bone cleaning composition comprises:
   i) a detergent having a functionality of the nature of a polyoxyethylene-4-lauryl ether
   ii) a detergent having a functionality of the nature of oxyethytlated alkylphenol, and
   iii) water,
      wherein said detergent having a functionality of the nature of a lauryl ether and said detergent having a functionality of the nature of oxyethylated alkylphenol are present in a weight percent ration of about 1:2, and wherein said composition does not contain a membrane stabilizer.

25. A soft tissue graft produced by the process as claimed in claim 24, wherein said graft is essentially free from bacterial, viral and fungal contamination.

26. A method for producing a soft tissue graft suitable for transplantation into a human, comprising:
   pre-cleaning said graft with water to produce a pre-cleaned graft;
   agitating said pre-cleaned graft in water optionally including one or more bone cleaning compositions to produced an agitated graft;
   sonicating said agitated graft in one or more bone cleaning compositions to produce a cleaned graft;
   incubating said cleaned graft in one or more decontaminating agents to produce a decontaminated graft;
   wherein said decontaminated graft is suitable for transplantation into a human.

27. A method for producing a soft tissue graft optionally attached to bone suitable for transplantation into a human, comprising:
   sonicating said soft tissue using an ultrasonic cleaning device with a first solvent comprising one or more detergents to produce a first cleaned soft tissue graft, said first cleaned soft tissue graft us essentially free from blood deposits;
   sonicating said first cleaned soft tissue graft using an ultrasonic cleaning device with a second solvent comprising one or more members selected from the group consisting of: an antibiotic, an antimycotic and an antiviral agent, to produce a second cleaned soft tissue graft; and
   sonicating said second cleaned soft tissue graft using an ultrasonic cleaning device with a third solvent comprising one or more decontaminating agents to produce a third cleaned soft tissue graft.

28. A method for producing a soft tissue graft optionally attached to bone suitable for transplantation into a human, comprising:
   sonicating said soft tissue using an ultrasonic cleaning device with a first solvent comprising one or more detergents to produce a first cleaned soft tissue graft, said first cleaned soft tissue graft us essentially free from blood deposits;
   agitating said first cleaned soft tissue graft with a second solvent comprising one or more members selected from the group consisting of: an antibiotic, an antimycotic and an antiviral agent, to produce a second cleaned soft tissue graft; and
   agitating said second cleaned soft tissue graft with a third solvent comprising one or more decontaminating agents to produce a third cleaned soft tissue graft.

* * * * *